United States Patent [19]

Jaeger

[11] Patent Number: 4,763,669
[45] Date of Patent: Aug. 16, 1988

[54] SURGICAL INSTRUMENT WITH ADJUSTABLE ANGLE OF OPERATION

[76] Inventor: John C. Jaeger, 3584 Batavia-Elba TLR, Oakfield, N.Y. 13125

[21] Appl. No.: 93,009

[22] Filed: Sep. 4, 1987

Related U.S. Application Data

[63] Continuation-in-part of Ser. No. 817,290, Jan. 9, 1986, abandoned.

[51] Int. Cl.⁴ ............................................. A61B 10/00
[52] U.S. Cl. .................................... 128/751; 128/305; 128/321; 30/251
[58] Field of Search ......................................... 128/4-8, 128/305-314, 321-323, 751, 752, 757, 758; 30/231, 242, 251

[56] References Cited

U.S. PATENT DOCUMENTS

| | | | |
|---|---|---|---|
| 1,823,199 | 9/1931 | Huxman | 30/251 |
| 2,293,984 | 8/1942 | Kirschbaum | 128/323 |
| 3,840,003 | 10/1974 | Kumiya | 128/751 |
| 4,243,047 | 1/1981 | Olsen | 128/751 |
| 4,522,206 | 6/1985 | Whipple et al. | 128/305 |
| 4,572,185 | 2/1986 | Rich | 128/322 |

FOREIGN PATENT DOCUMENTS 439303 12/1935 United Kingdom ................. 30/251

*Primary Examiner*—Max Hindenburg
*Attorney, Agent, or Firm*—Lalos & Keegan

[57] ABSTRACT

A surgical instrument for obtaining biopsies, performing microsurgery and bipolar microelectrocautery. The instrument head includes opposing jaw members which open and close during the operating procedures. The angle of the instrument head relative to the instrument frame is adjustable to effectively operate on varying surfaces. The angle can be continuously adjusted while the instrument is in an operating position.

17 Claims, 5 Drawing Sheets

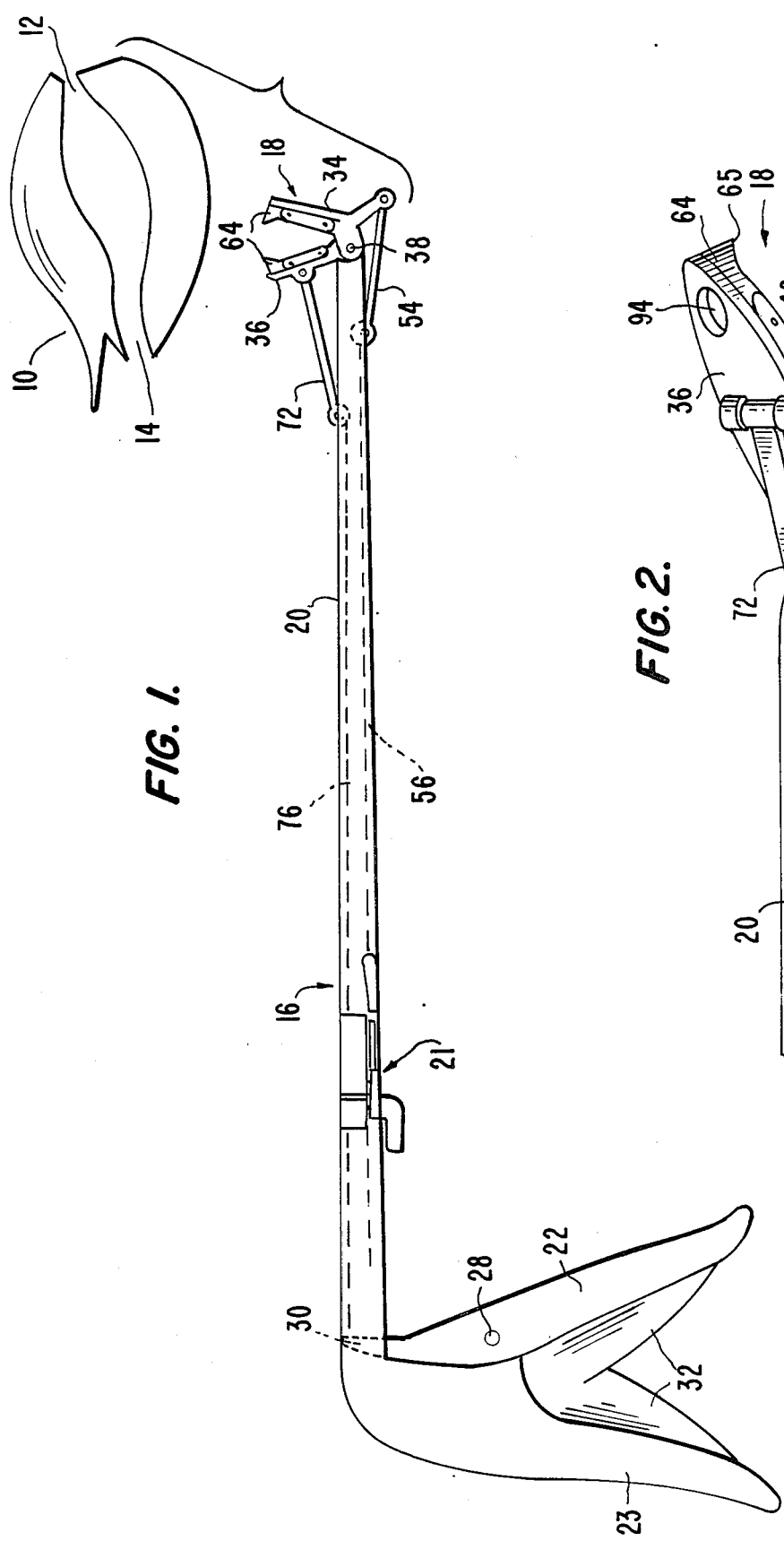
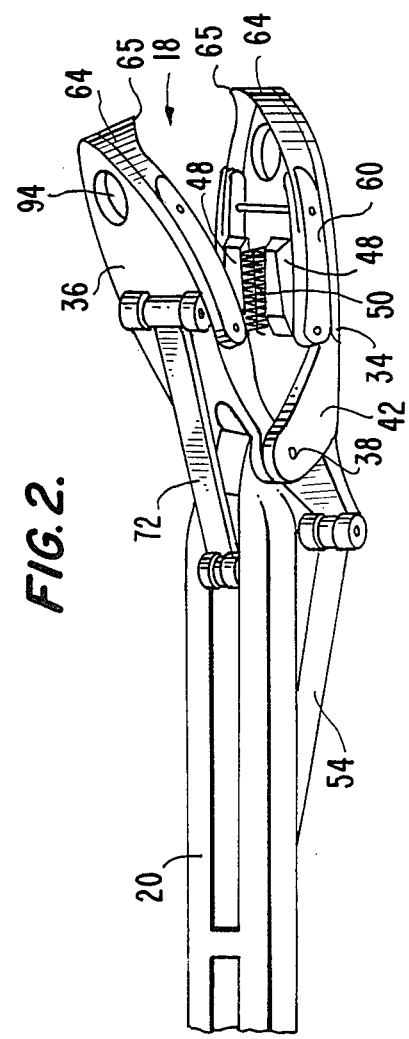
FIG. 1.
FIG. 2.

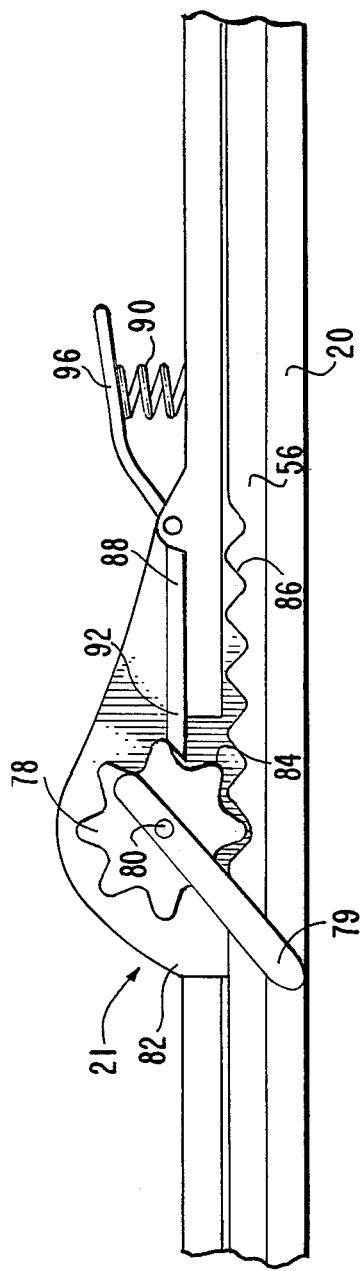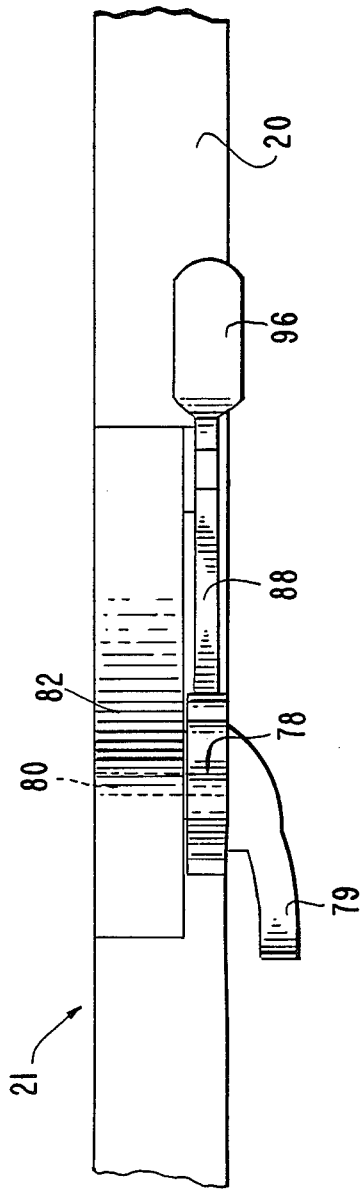

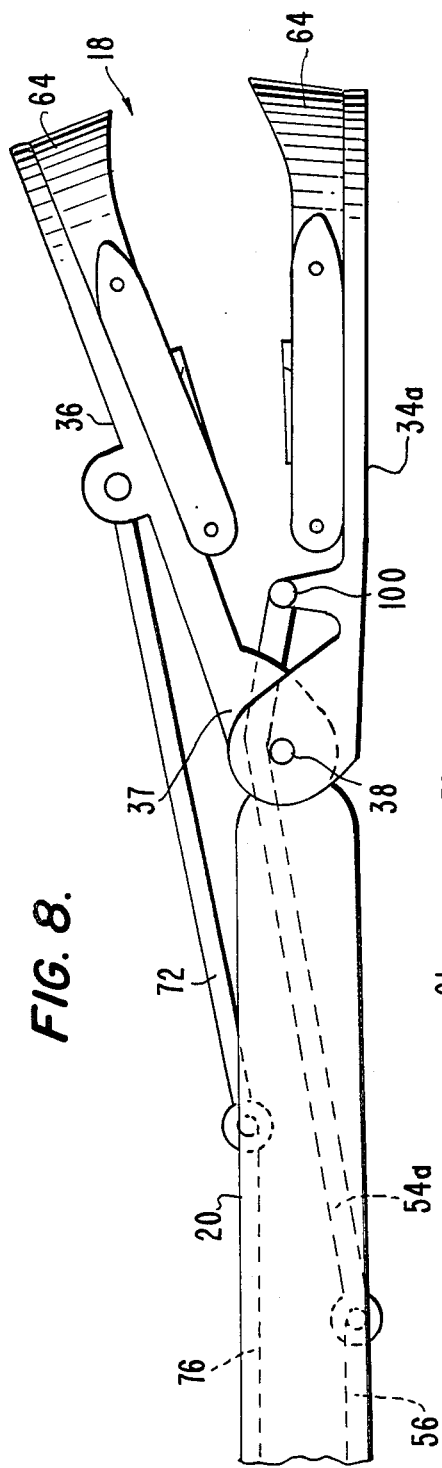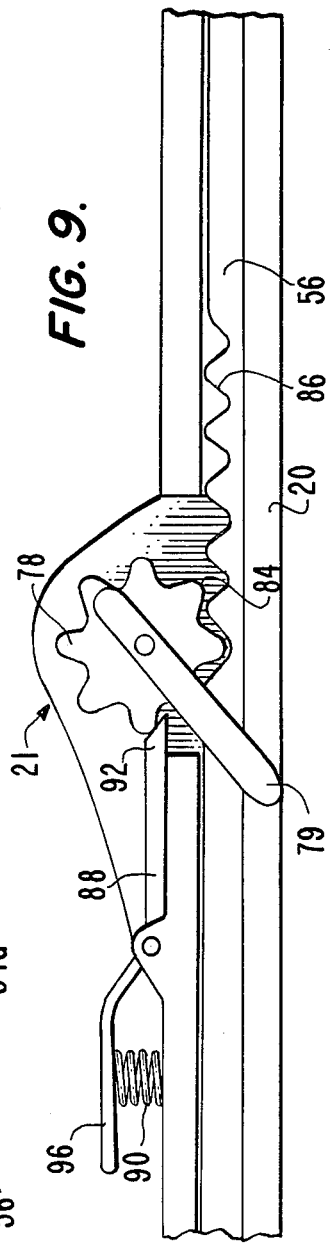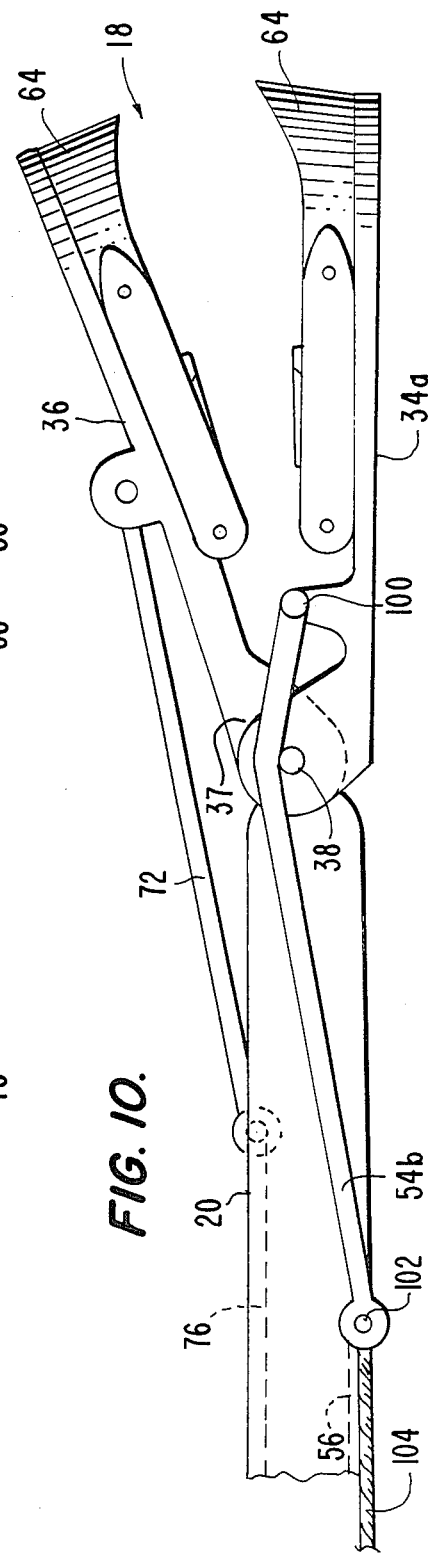

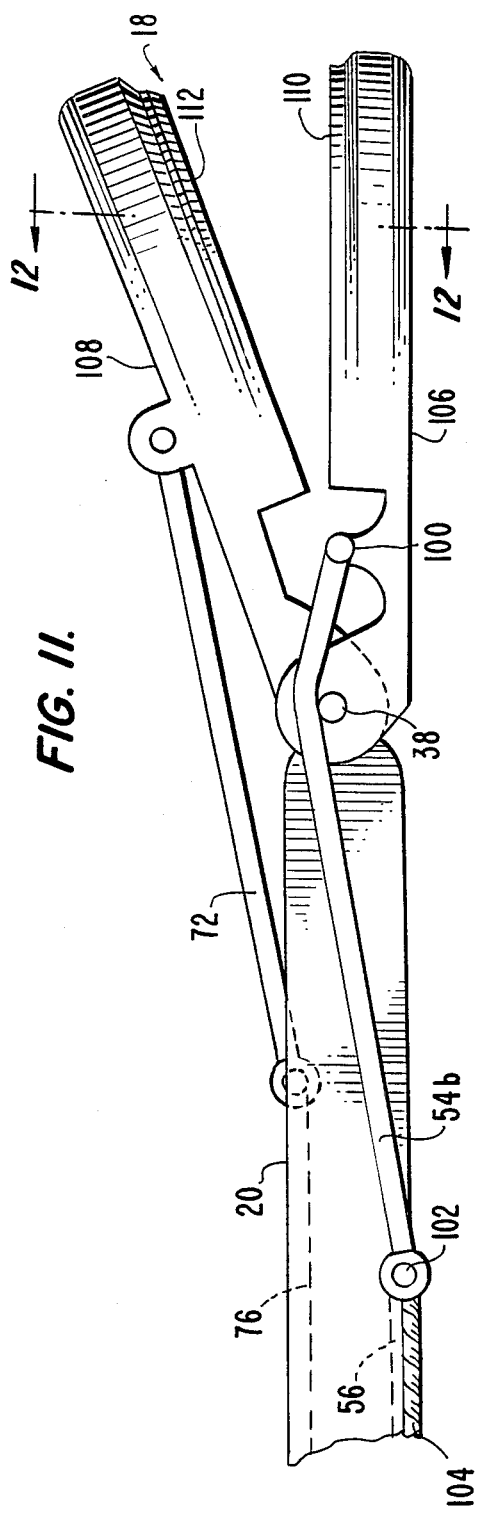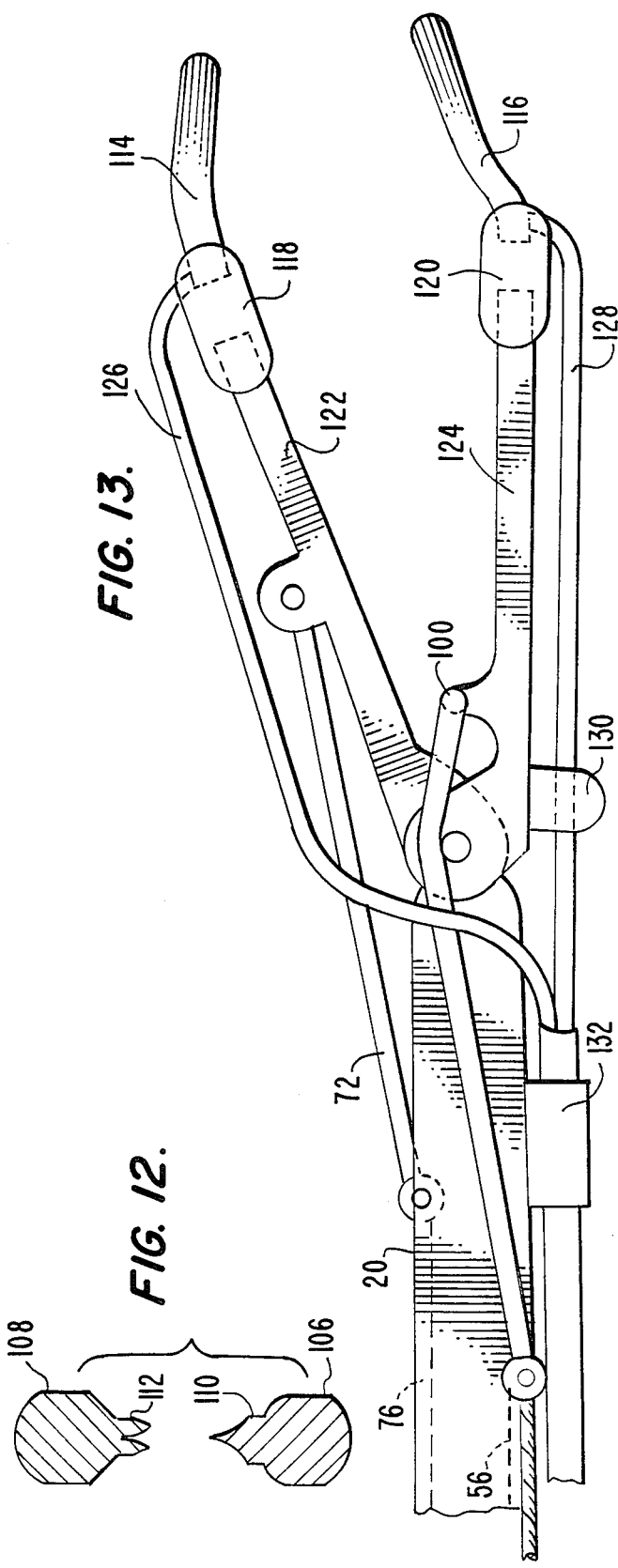

SURGICAL INSTRUMENT WITH ADJUSTABLE ANGLE OF OPERATION

RELATED APPLICATIONS

This application is a continuation-in-part of U.S. application Ser. No. 817,290, filed Jan. 9, 1986, now abandoned.

BACKGROUND OF THE INVENTION

The present invention relates generally to medical devices, and more particularly, to devices for obtaining biopsies, for performing microsurgery and bipolar microelectrocautery. The angle of operation can be varied to permit operation on curved and sloped surfaces.

Conventional instruments for obtaining biopsies from the uterine cervix and the vagina are used, for example, in gynecology for the diagnosis of cervical intraepithelial neoplasia (CIN) which is a non-invasive surface cancer and its precursors. Cervical biopsies of the uterine cervix and of the vagina are common procedures in gynecology.

Cervical biopsies are usually performed after inspection of the cervix through a colposcope (a binocular for magnification and identification of small areas of abnormality). During colposcopic examination, acetic acid is applied on the cervical surface making the area to be biopsied identifiable, even through the unarmed eye, by whitish discoloration. The cervical surface is thereby "mapped out" rather accurately.

However, conventional instrments do not permit an accurate biopsy to be taken. A major disadvantage of conventional instruments is that the angle of the cutting head in relation to the instrument frame cannot be varied and these instruments do not allow access to cervical lesions at variable angles of approach for a directed biopsy. This would be desirable since the lesions commonly are located either on the lateral slope of the cervix or on its slope towards the endocervical canal. Therefore, it can be difficult, if not impossible, to obtain adequate biopsy specimens with conventional instrments that take "bites" only in a straight forward direction.

The present invention overcomes this disadvantage by providing an adjustable instrument head with which the angle of operation can be varied to permit operation on curved or sloped surfaces.

Other medical instruments have been suggested in which the relative angle of the foremost part of the instrument is adjustable. However, these instrm ents are not useable or applicable for obtaining biopsies, performing microsurgery or microelectrocautery. Further, a disadvantage of these instruments is that the angle is not easily adjusted while the instrument is being used.

This is a major disadvantage in certain operations, e.g. a laparoscopic procedure, in which a variety of sequential operative functions must be performed. These functions include bipolar electrocautery of surface lesions occupying various surface areas, bipolar electrocautery of violin string adhesions, and bipolar electrocautery of ahesion sheets and sheaths. These adhesions and lesions may be located on various planes since they commonly involve surfaces of the Fallopian tubes and the ovaries which have cylindrical and spheroid surfaces, respectively.

The present invention overcomes this major disadvantage by including an angle adjustment bar that can easily be manipulated to change the angle of the instrument while the instrument is being held and used. Further, angle adjustments can actually be made by squeezing the handles of the instrument. These unique angle adjustment features make the present invention ideally suited for operations with sequential procedures requiring varying angles of approach.

An added disadvantage of most conventional instruments for obtaining biopsies is that they do not possess exchangeable knife blades. Instruments which do have replaceable blades frequently cannot cut through the tissue of the cervix, particularly if it is of relatively firm consistency. The blades of these instruments can actually be bent out of shape during an attempted biopsy.

Instruments with non-exchangeable knife blades require periodic resharpening which means sending the instrument back to the manufacturer, and this creates added expense as well as loss of use of the instrument.

OBJECTS OF THE PRESENT INVENTION

The object of the present invention is to provide a forceps-type instrument which eliminates the disadvantages of the prior art devices for obtaining biopsies from the cervix or for performing relatad-surgery.

Another object of the invention is to provide a forceps-type instrument in which the instrument head is pivotable so that the angle of approach of the head (with blades, scissors, or electrodes) to the tissue may be varied.

Another object of the invention is to provide an instrument in which the angle of the instrument head can be easily adjusted while the instrument is in use.

It is another object of the present invention to provide a forceps-type biopsy instrument in which the blades can be removed for sharpening and then replaced.

It is a further object of the invention to provide an instrument in which the blade is both exchangeable and sturdy so that it does not bend even when tissues of relatively firm consistency are being cut.

Another object of the invention is to provide a forceps-type microsurgery instrument with remotely directable scissors on the instrument head.

A further object of the invention is to provide a forceps-type microelectrocautery instrument with remotely directable metal electrodes.

Other objects and advantages of the present invention will become more apparent to those persons having ordinary skill in the art to which the invention relates from the following description taken in conjunction with the accompanying drawings.

DESCRIPTION OF THE DRAWINGS

FIG. 1 is a view of the entire forceps-type instrument of the present invention in place within the vagina and adjacent the cervix, with the blade jaws in the 90° position.

FIG. 2 is a perspective view of the cutting head of the instrument in its straightforward position.

FIG. 6 is a detail view of the push rod moving mechanism for adjusting the angle of approach of the blades to the tissue.

FIG. 7 is a detail plan view of the mechanism in FIG. 6.

FIG. 8 is an elevational view of the instrument showing an alternate linkage arrangement for controlling the position of the lower jaw member.

FIG. 9 is a detail view of an alternate arrangement of the push rod mechanism operable with the linkage arrangement of FIG. 8.

FIG. 10 is an elevational view of the instrument showing another alternate linkage arrangement for controlling the position of the lower jaw member.

FIG. 11 is an elevational view of the instrument with scissor blades mounted on the instrm ent head for microsurgery.

FIG. 12 is a cross-sectional view of the cooperative scissor blades of FIG. 11.

FIG. 13 is an elevational view of the instrument with electrodes mounted on the instrument head for microelectrocautery.

DESCRIPTION OF THE PREFERRED EMBODIMENT

The uterus in a female is a pear-shaped organ with four distinguishable sections. Portions are shown in FIG. 1. A portion of the body called the corpus uteri 10 is shown having a rounded upper end. The endometrial cavity 12 is shown as is the cervix uteri 14 which opens into the vagina.

Figure 3:
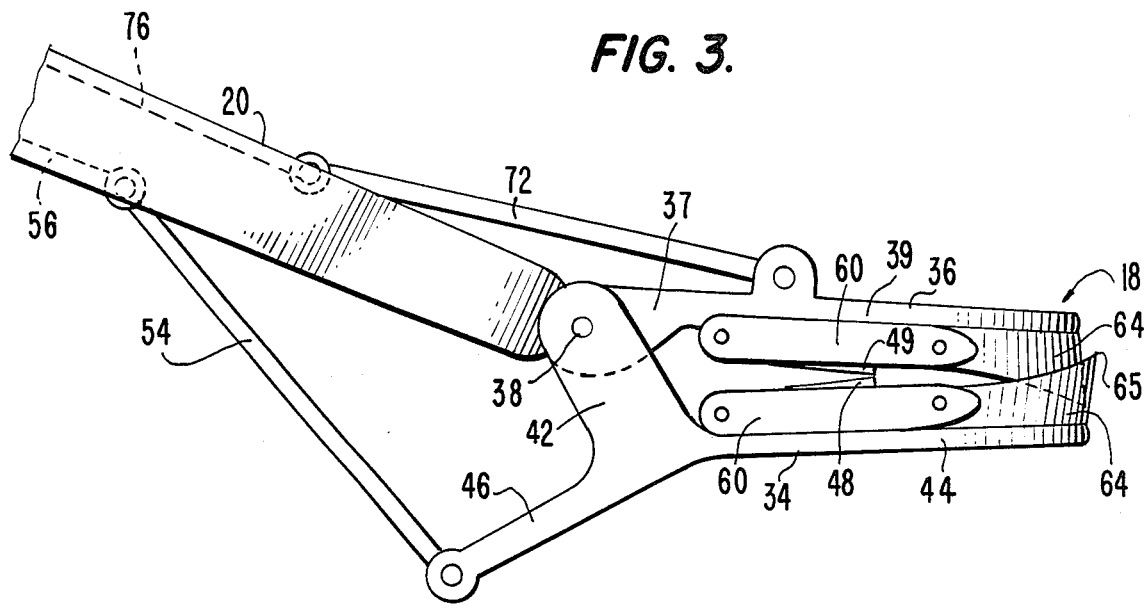
FIG. 3 is an elevational view of the device showing it in closed position as when a biopsy is taken.

The forceps-type instrument 16 must pass through the vagina to the cervix, and then depending upon what area of the cervix the biopsy is to be taken from, the cutting jaw blades 64 will be adjusted to the appropriate angle of approach. FIG. 1 shows cutting jaw blades 64 in the 90° position with respect to the frame 20 of instrument 16, in which position it may take biopsies from the lateral portions of the cervix uteri, or from a slope area toward the cervical canal. The jaw blades 64 can be further manipulated to a 150° position with respect to the frame. This retrograde or backward position of jaw blades 64 is useful in certain specialty procedures. Any further movement toward a 180° position is of course limited by the frame of the instrument itself. FIGS. 2 and 3 show the cutting blade jaws in the straight forward position from which position biopsies may be taken from the front of the cervix uteri which opens into the vagina.

The instrument 16 (FIG. 1) comprises four basic parts including frame 20, cutting head 18, angle adjustment mechanism 21, and handles 22 and 23. The frame 20 is made of any suitable material, such as stainless steel, and houses two push rods 56 and 76 slidably mounted in longitudinal notches (not shown). push rods 56 and 76 move jaw levers 54 and 72, respectively, and thus move the jaws and blades toward and away from one another. push rod 56 controls and varies the position of the pivoting jaw 34 of head 18 from a straight forward position as shown in FIGS. 2 and 3 to a nearly 90° lateral position as shown in FIG. 1. push rod 76 controls and varies the position of pivoting jaw 36 from closed position as shown in FIG. 3 to an open position as shown in FIG. 1.

The frame 20 is connected together with the first handle 23 fixed to the frame and the second handle 22 pivotally mounted to the frame by a pin 28 so that when the handles are pressed toward one another the top 30 of the second handle 22 moves toward cutting head 18 to move push rod 76 to the right as viewed in FIG. 1 to close the jaws of the cutting head to cut tissue. The handles are normally kept in the spread apart position as shown in FIG. 1 by a recoil spring 32.

As shown more clearly in FIG. 2 and 3, the cutting head 18 includes two jaws 34 and 36 each of which is pivotally mounted on a pin 38 mounted to frame 20. Thus, the jaws may be moved toward and away from one another by squeezing handles 22 and 23 together. They are shown together (closed) in FIG. 3 and open in FIGS. 1 and 2. An important feature of the present invention is that the handles are also used to change the angle of the jaws 34 and 36 in relation to the frame.

The angle adjusting device 21 moves the jaws between the position of the jaw angles shown in FIGS. 2 and 3, to the jaw angle shown in FIG. 1. The straight forward position shown in FIGS. 2 and 3 is used during insertion into and removal from the vagina, and either the instrument is used in this position or the angle is adjusted after the instrument has been inserted into the vagina and is in place to take the biopsy. The handles are also used to adjust the angle as will be explained later in detail.

Referring to FIGS. 2 and 3, each jaw forms a lever which pivots about pin 38. Force is applied to jaw 34 through lever arm 54 and force is applied to jaw 36 through lever arm 72. The opposing directed forces of lever arms 54 and 72 enhance the surgical action (grasping, cautery, biopsy, cutting) of the instrument.

Jaw 34 is pivoted to the frame 20 by a crank arm 42. Jaw 34 also has a blade arm 44 and a control arm 46. Blade arm 44 includes a stop block 48 mounted on one side which forms a part of the interior of cutting head 18. Block 48 is for arresting closure of the knife blades 64 as shown in FIG. 3. Block 48 has a spring 50 (FIG. 2) for retaining blade 64 in a fixed position as will be later described in greater detail. At the forward end of arm 44 (FIG. 4) there is a slot 52 for receiving knife blade 64. Control arm 46 is pivotally connected to lever arm 54 which is in turn connected to push rod 56. Push rod 56 is mounted for slidable movement within the frame 20, as for example in a longitudinal notch, so that jaw 34 can be moved from a straight position to a 150° position depending upon the desired angle of approach. The mechanism for changing this angle will be later described in detail.

Jaw 36 is pivoted to frame 20 by crank arm 37 (FIG. 3). Similar to jaw 34, jaw 36 has a blade arm 39. Blade arm 39 also contains a stop block 49, a spring (not shown) and a blade receiving slot (not shown). Blade arm 39 is pivotally connected to lever arm 72 which is in turn connected to push rod 76. Push rod 76 is mounted for slidable movement within frame 20 so that jaw 36 can be moved toward and away from jaw 34 by squeezing or releasing handles 22 and 23.

The knives 140 (FIG. 5) are similar to each other in construction and include a jaw frame 58 having sides 60 and a spar 62 across the front and a spar 63 across the rear of the sides so that a generally rectangular frame is formed. The razor-edged knife blade 64 itself is fixed to the frame 58 and has a lip 66 (FIG. 5) at the front end on its non-cutting side which fits into the slot 52 (FIG. 4) in jaw 34 or 36 to mount the blade 64 and frame 58 to the front of the jaw. The cutting side of the razor-edged knife blade is shaped as shown in FIGS. 2 and 3 and has a sharp penetrating portion or tip 65. The ends of the two opposing blades cooperate to take a "bite" at the tissue, and as the blades close further they separate the tissue from the body part from which the biopsy is being taken. Each blade curves rearwardly away from the sharp tip 65.

Each jaw 34 and 36 contains identical structure for receiving and maintaining each knife 140 in position. For simplicity, only the structure related to jaw 34 will be described.

Figure 4:
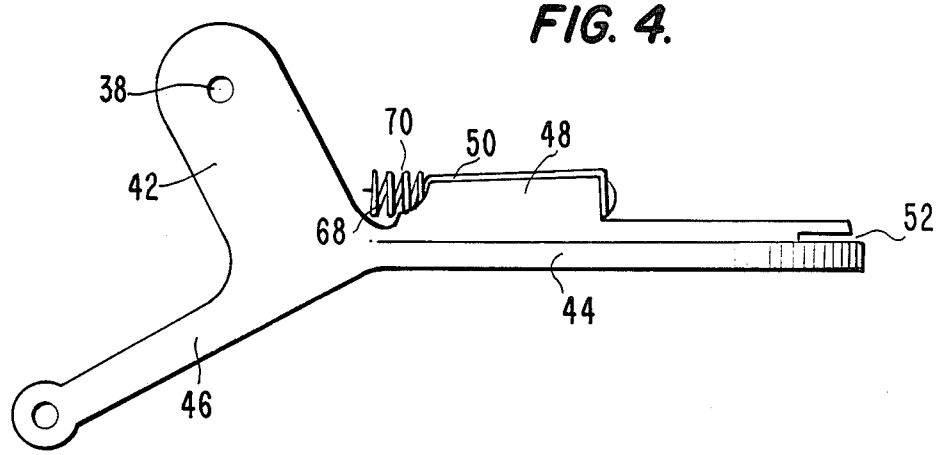
FIG. 4 is an elevational view of the main forceps jaw.
Figure 5:
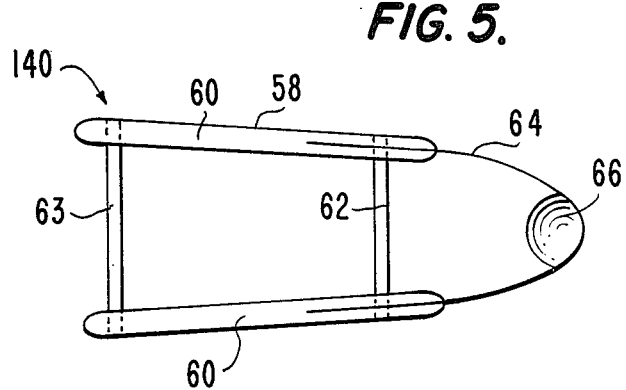
FIG. 5 is a bottom view of the blade in its frame ready to be inserted into a jaw.

Referring to FIGS. 4 and 5, the knife rear spar 63 slips into the notch 68 formed at the junction of the crank arm 42, blade arm 44 and the back 70 of the spring 50 on stop block 48. The rear spar 63 actually snaps into place and can be easily removed by pressing against the back part 70 of the spring with a suitable instrument. The spar 63 can then be lifted out of notch 68 since it is no longer being held in place by spring 50.

The knife blades 64 may be fixed in the frame 58 in a suitable manner such as by soldering, welding, riveting, or a press fit, and a knife blade and frame together may be a single exchangeable unit. The base portions of the jaws 34 and 36 are not identical in length, but rather of such dimensions to allow the closure of the identical knives as shown in FIG. 3. The jaws 34 and 36 are slightly asymmetrical in that the location of the knife frame 58 on jaw 36 is slightly more to the rear than on the jaw 34. The two frame-knife units are identical and interchangeable.

The knife blades are in the closest possible position as shown in FIG. 3 and the rearward spar is retained in position by spring 50 and particularly its back portion 70 (FIG. 4). In the closed position of the knives (FIG. 3), the sharp tip 65 of the upper blade is received within the lower blade.

Relative movement of the two jaws 34 and 36 will now be described. As will be appreciated from the following discussions, jaw 34 is moved to vary the angle at which the instrument head 18 approaches the surface to be operated upon. With jaw 34 in a stationary position, at a fixed angle of approach, jaw 36 is moved to close or open the instrument head 18 by bringing the jaws 34 and 36 together or moving them apart.

Jaw 36 is pivotally connected to frame 20 at pin 38. Jaw lever 72 is connected to a midpoint of jaw 36 as shown in FIG. 2. Jaw lever 72 is connected at its other end to push rod 76 slidably mounted in frame 20 (FIG. 3). Push rod 76 is connected at its other end to handle 22 (FIG. 1). When handle 22 is squeezed toward handle 23 (fixed to frame 20), the upper end 30 of handle 22 (pivotally connected to handle 23) causes forward motion of push rod 76. The force of push rod 76 is transferred to jaw 39 through lever 72 causing the head 18 to close into the cutting position. Through the action of recoil spring 32 (FIG. 1), releasing handle 22 will cause jaw 39 to return to an open position as shown in FIGS. 1 and 2.

The mechanism 21 for changing the position of the jaws with respect to the longitudinal direction of frame 20 is shown in detail in FIGS. 6 and 7. Mechanism 21 includes gear wheel 78 to which a bar 79 is connected. Movement of bar 79 will rotate gear wheel 78 about pin 80 on which gear wheel 78 is mounted. Pin 80 is mounted in protective housing 82. Housing 82 is slightly larger than gear wheel 78 so that gear wheel 78 will not contact and possibly cause injury to the delicate vaginal tissues. Gear wheel 78 includes teeth 84 on its periphery which engage and cooperate with matching teeth 86 on slidable push rod 56. When bar 79 is moved clockwise, push rod 56 is moved longitudinally to the left as seen in FIG. 6. Conversely, when bar 79 is moved counterclockwise, push rod 56 is moved longitudinally to the right. Movement of push rod 56 moves lever arm 54 (FIG. 3) and thus jaw 34 as previously described. Jaw 34 pivots about pin 38 thereby changing the angle of head 18 with respect to frame 20, between the straight forward position shown in FIGS. 2 and 3 and the 90° position as shown in FIG. 1, and further to a 150° position, not shown.

Rearward displacement (i.e., to the left in FIGS. 6 and 7) of push rod 56 requires disengagement of end 92 of arrest member 88 from gear wheel teeth 84. Disengagement of end 92 is accomplished by downward pressure of handle portion 96, thus compressing spring 90.

With end 92 disengaged, push rod 56 can be rearwardly displaced by moving bar 79 clockwise. However, during an operation it may be inconvenient for an operating physician to use one hand to push down handle portion 96 while using the other hand to turn bar 79. However, with the arrangement of the present invention, bar 79 does not have to be used to move push rod 56. Instead, squeezing handles 22 and 23 will accomplish the same result, as will be explained. This important feature of the present invention permits the physician to maintain control of the instrument with handles 21 and 22 while simultaneously adjusting the angle of head 18.

With end 92 of arrest member 88 disengaged, squeezing handle toward handle 23 will cause jaw 36 to move to a closed position against jaw 34 as previously described. As handle 22 is squeezed further, jaw 36 will begin to push against jaw 34 moving it clockwise about pin 38 (FIG. 3) thus causing rearward displacement of push rod 56 under the force of lever 54.

The position of head 18 relative to frame 20 can be changed in a clockwise direction by pressing down on handle portion 96 while squeezing handles 22 and 23. The position of head 18 can be changed in a counterclockwise direction by simply moving bar 79 counterclockwise. In each instance, the operating physician can continue to hold the instrument by handles 22 and 23.

A typical operation with the instrument of the present invention will now be described. When it is desired to take a selective biopsy, the instrument 16 is advanced into the vagina, to the cervix, while in the straight forward position and is then positioned so that jaws 34 and 36 are at the correct angle with respect to the tissue from which the biopsy is to be taken. For example, as shown in FIG. 1, the biopsy is being taken either on a slope portion toward the cervical canal or on the lateral portion of the cervix and therefore jaws 34 and 36 are in the 90° position with respect to the longitudinal direction of frame 20. Initially, cutting head 18 is advanced toward the cervix with jaw 34 in the straight forward position. One hand holds the handles 22 and 23 while the other hand is free to rotate bar 79 counterclockwise (FIG. 6), in order to move jaw 34 counterclockwise to the position shown in FIG. 1. Counterclockwise rotation of gear wheel 78 (FIG. 6) is possible without prior compression of spring 90 since teeth 84 slide by end 92 while elevating it.

During an operating procedure, it would be cumbersome to rotate bar 79 and simultaneously hand compress spring 90 to adjust cutting head 18 clockwise. As previously discussed, the present invention obviates this problem. Initially, an operating physician initiates a trial approach of cutting head 18 toward the specific area that is to be biopsied, including a partial trial closure of the forceps jaws without actually cutting into the tissue. If as a result of that trial, it is apparent that a more straight forward direction of cutting head 18 would be more suitable than the one chosen initially, the position of cutting head 18 can then be adjusted clockwise (again as viewed in FIG. 1). As previously discussed, clockwise rotation of gear wheel 78 (FIG. 6) is possible only after disengagement of end 92 from gear wheel 78. Disengagement requires compression of spring 90. As discussed above, once spring 90 is compressed, handles 22 and 23 are squeezed to initially move jaw 36 to a closed position against jaw 34. As handles 22 and 23 are squeezed further, jaw 36 will push the jaw 34 to a more forward directed position. The final position of jaws 36 and 34 will of course depend on how long the physician continues to squeeze handles 22 and 23. This final selected position will be maintained by the cooperation of gear wheel teeth 84 and 86 after compression of spring 90 is discontinued and end 92 is reengaged. The jaws are normally in the open position when at the angle shown in FIG. 1 or the angle shown in FIG. 2. In order to take a biopsy, the jaws are closed by squeezing handles 22 and 23 toward one another. This moves push rod 76 to the right as seen in FIG. 1 and pushes lever 72 forward thereby moving jaw 36 toward jaw 34 which closes the jaws and cuts the desired tissue to provide the biopsy. Jaw 34 remains stationary in the selected position due to the action of end 92 of arrest member 88. The bases of both jaws 34 and 36 have openings 94 suitable for removal of the biopsy specimen with a Q-tip or similar device.

By way of example, the approximate length of frame 20 is 25 to 30 cm. The distance of the angle adjustment mechanism 21 from cutting head 18 should be great enough to permit rotation of bar 79 or depression of handle portion 96 while the instrument is positioned in the vagina. The approximate length of jaw 34 is 1.0 to 1.5 cm and the knife frame 58 has an approximate length of 0.8 to 1.2 cm and width of 0.3 to 0.5 cm. The length of the handles is about 9 to 12 cm.

Numerous modifications can be made without departing from the spirit and scope of the present invention. FIG. 8 illustrates one such alternative embodiment in which jaw 34 (FIGS. 3 and 4) has been replaced with a simpler jaw 34a, similar in construction to jaw 36. In the embodiment of FIG. 8, control arm 46 (FIGS. 3 and 4) has been eliminated and jaw lever 54 (FIG. 3) has been replaced with angled jaw lever 54a. Jaw lever 54a is connected at one end to push rod 56 and pivotally connected at its other end to pin 100 mounted on jaw 34a. Jaw lever 54a moves through a hollow section of frame 20 and an opening in crank arm 37 of jaw 36 under control of push rod 56.

As will be appreciated from FIG. 8, forward motion (to the right) of push rod 56 will cause jaw 34a to be lowered (or move clockwise). This effect is opposite to that achieved by the first embodiment of jaw lever 54 and jaw 34 shown in FIGS. 3 and 4. The opposite effect of push rod 56a requires a modification to the angle adjustment mechanism 21. As shown in FIG. 9, arrest member 88 with end 92, handle portion 96, and spring 90 are now mounted on the left side of gear wheel 78. In the embodiment of FIGS. 8 and 9, forward displacement (i.e., to the right in the Figures) of push rod 56 now requires disengagement of end 92. The effect of squeezing handles 22 and 23 with end 92 disengaged is still to move jaw 34a clockwise as previously described with reference to the embodiments shown in FIGS. 3 and 6.

FIG. 10 illustrates another alternative embodiment of the present invention in which the single jaw lever 54a of FIG. 8 is replaced by two jaw levers 54b mounted on the exterior of frame 20. FIG. 10 illustrates one jaw lever 54b. The second jaw lever 54b (not shown) is located on the opposite side of instrument 16. Both jaw levers 54b are structurally the same and mounted in the same manner but on opposite sides of instrument 16. The arrangement of FIG. 10 obviates the need for a hollow section in frame 20 or an opening in crank arm 37 as is required in the arrangement of FIG. 8. Each jaw lever 54b is pivotally connected at one end to a pin 100 mounted to the outside surface of jaw 34a. Jaw lever 54b is pivotally connected at its other end to pin 102 mounted for movement within slot 104 in frame 20. Push rod 56 is connected to pin 102 and acts to move jaw lever 54b in the same manner as previously described with respect to jaw lever 54a.

The embodiment of FIG. 10 with jaw lever 54b and jaw 34a provides significant advantages over the configuration of FIG. 3 with jaw lever 54 and control arm 46. By eliminating control arm 46, the instrument is ideally suited for biopsies of any part of the cervix or vagina in that the instrument will not interfere or contact other parts of the cervix or vagina.

Further, the configuration of FIG. 10 is critical when using the instrument during a laparoscopy wherein the instrument must be advanced through a cannula into the patient's abdominal cavity. By eliminating extension 46, the cross section of the instrument head, with both jaws in the straight forward position, can easily be made smaller than the cross section of the main frame, thus making the instrument insertable through a cannula.

FIG. 11 illustrates an alternative embodiment of the present invention in which jaws 34 and 36 of cutting head 18 have been replaced with scissor blades 106 and 108. The scissor blade arrangement of FIG. 11, utilizing the cutting angle features of the present invention, provides a unique microscissor tool for microsurgery. The scissor blades 106 and 108 can be varied in shape, size and strength to suit the requirements of various operations.

FIG. 12 illustrates one configuration of scissor blades 106 and 108 in which single-edged cutting section 110 of blade 106 is received within doubled-edged cutting section 112 of blade 108. The shape of the cooperating cutting sections 110 and 112 inhibits lateral displacement. This embodiment meets a specific surgical requirement in cutting very sturdy tissues, such as the vagina.

FIG. 13 illustrates yet another embodiment of the present invention in which the scissor blades 106 and 108 of FIG. 11 have been replaced with electrodes 114 and 116. The size and shape of electrodes 114 and 116 can be varied to meet particular surgical requirements. For example, microcautery would require very thin electrodes. Electrodes 114 and 116 are attached to insulator sections 118 and 120 which are in turn removably attached to instrument jaw members 112 and 124.

The angle adjustment and open/close movement of jaw members is the same for jaw members 122 and 124 as that previously described in connection with jaws 36 and 34a. Electrical current is delivered to electrode 114 through electrical lead 126 and to electrode 116 through electrical lead 128. Lead guide 130 is provided on jaw member 124 and cable guide 132 is provided on frame 20. Cable 134, with electrical leads 126 and 128, is connected to an appropriate electrical supply (not shown).

From the foregoing, it will be evident to one having ordinary skill in the art that many other modifications and enhancements can be made without departing from the spirit and scope of the present invention.

I claim:

1. A medical instrument for performing surgical procedures, comprising:
    a longitudinal instrument frame;
    an instrument head connected to a first end of said frame, said head including two jaw members connected to said frame for relative movement toward and away from each other;
    a handle means connected to a second end of said frame for holding said instrument frame and connected to said head for moving at least one of said jaw members;
    means connected to said frame and said head for adjusting the angular position of said head relative to said frame in a fixed plane, said relative movement of said jaws occurring in said fixed plane; and
    said adjusting means including said handle means.

2. An instrument as defined in claim 1 in which said adjusting means further includes a bar for adjusting the angular position of said head in a first direction and a second direction, said second direction being opposite to said first direction.

3. An instrument as defined in claim 2 in which said handle means adjusts the angular position of said head in said second direction.

4. An instrument as defined in claim 3 in which said adjusting means includes a rotating means which rotates in said first and second directions in response to movement of said bar.

5. An instrument as defined in claim 4 in which said rotating means is coupled to a first means for changing the relative angular position of a first one of said jaw members relative to said frame.

6. An instrument as defined in claim 5 in which said handle means is coupled to a second means for changing the angular position of a second one of said jaw members relative to said frame.

7. An instrument as defined in claim 6 in which said adjustment means includes means for engaging said rotating means and for arresting movement of said rotating means in said second direction thereby inhibiting said first changing means from changing said relative angular position of said first jaw member in said second direction.

8. An instrument as defined in claim 7 in which disengagement of said arresting means enables said handle means to change the angular position of said second jaw member and the angular position of said first jaw member after said first and second jaw members have been moved together by said handle means.

9. An instrument as defined in claim 1 in which each of said jaw members includes a cutting blade.

10. An instrument as defined in claim 9 in which said cutting blades are razor-edged blades.

11. An instrument as defined in claim 10 in which each said razor-edged blade includes a sharpened tip and the tip of one of said blades on a first jaw member slides next to and past the tip of a second blade on a second jaw member when said jaw members are closed together.

12. An instrument as defined in claim 10 in which said razor-edged blades are removably attachable to said jaw members.

13. An instrument as defined in claim 10 in which said cutting blades are scissor blades.

14. An instrument as defined in claim 13 in which a first one of said scissor blades is double-edged and a second one of said scissor blades is single-edged such that the single-edged scissor blade fits within the double-edged scissor blade when said jaw members are closed together.

15. An instrument as defined in claim 1 in which each of said jaw members includes an electrode.

16. An instrument as defined in claim 15 in which said electrodes are removably attachable to said jaw members.

17. An instrument as defined in claim 16 in which said electrodes are attached to electrical leads for supplying electrical current to said electrodes.

* * * * *